United States Patent [19]

Weyer et al.

[11] 4,221,815
[45] Sep. 9, 1980

[54] BENZOIC ACIDS, THEIR DERIVATIVES AND PROCESS FOR PREPARING THEM

[75] Inventors: Rudi Weyer, Kelkheim; Volker Hitzel, Lorsbach; Karl Geisen, Frankfurt am Main; Werner Pfaff, Hofheim, all of Fed. Rep. of Germany

[73] Assignee: Hoechst Aktiengesellschaft, Frankfurt am Main, Fed. Rep. of Germany

[21] Appl. No.: 646,378

[22] Filed: Jan. 2, 1976

[30] Foreign Application Priority Data

Jan. 3, 1975 [DE] Fed. Rep. of Germany ....... 2500157

[51] Int. Cl.$^2$ .................. A61K 31/195; C07C 101/72
[52] U.S. Cl. .................................... 424/319; 260/333; 260/345.7 R; 260/345.8 R; 260/346.71; 424/258; 424/263; 424/275; 424/278; 424/283; 424/285; 424/309; 546/168; 546/298; 549/64; 549/70; 549/72; 560/38; 560/42; 560/45; 560/47; 560/48; 562/442; 562/455; 562/456; 562/457; 562/458; 562/451

[58] Field of Search ............ 260/519, 518 R; 560/38, 560/42, 45, 47, 48; 562/442, 455, 456, 457, 458, 451; 424/319, 309, 316

[56] References Cited

U.S. PATENT DOCUMENTS

| 3,536,753 | 10/1970 | Gruenfeld | 260/519 |
| 3,636,094 | 1/1972 | Yonan | 260/518 R |
| 3,855,285 | 12/1974 | Holland | 260/516 |

FOREIGN PATENT DOCUMENTS

| 2088225 | 2/1972 | France | 260/519 |
| 900131 | 7/1962 | United Kingdom | 260/519 |

OTHER PUBLICATIONS

Williams et al., J. Chem. Soc., Perkin Trans., 2 (14), 2112-2115 (1972).

Primary Examiner—G. T. Breitenstein
Attorney, Agent, or Firm—Curtis, Morris & Safford

[57] ABSTRACT

Acyl-aminoalkyl-benzoic acid and derivates thereof show a blood sugar lowering effect upon oral administration and can be used as orally applicable hypoglycemiants.

12 Claims, No Drawings

BENZOIC ACIDS, THEIR DERIVATIVES AND PROCESS FOR PREPARING THEM

The present invention provides substituted benzoic acids, their salts and esters. The compounds are distinguished by a blood sugar lowering action.

It is known that sulfonamide derivatives such as sulfonyl-ureas, sulfonyl-semicarbazides, sulfonamido-pyrimidines and some other sulfonamide heterocycles as well as sulfonyl-urethanes show a blood sugar lowering action in a not pre-treated test animal. Some of these compounds are also used in human therapy for the treatment of diabetes mellitus. It has been found that, surprisingly, substituted benzoic acids, their salts and esters also provoke a lowering of the blood sugar level.

Accordingly, the present invention relates to benzoic acids and their derivatives having blood sugar lowering action, in particular to compounds of the general formula I

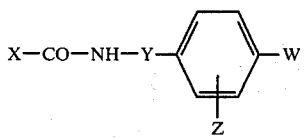

in which

W represents a carboxyl group or a salt or ester thereof

X represents an aromatic or heteroaromatic ring system,

Y represents a single chemical bond or a hydrocarbon bridge, and

Z represents hydrogen or one or several other substituents.

For the formation of salts of the carboxyl group that may be used as substituent W, there are suitable in the first instance the alkali metals and ammonium. However, other metals may also be used, for example alkaline earth metals. But, in view of the pharmaceutical use of the products, the use of the metals is limited to those which are physiologically tolerated.

For a possible esterification of the carboxyl group, on principle all alcohols may be used. The lower monohydric alcohols such as methanol, ethanol or propanol, and polyhydric alcohols, for example glycol, or alcohols with other functional groups such as ethanolamine or glycol ethers are preferred.

As the substituent X in the above formula, there may be used in the first instance mono-nuclear aromatic or heteroaromatic ring systems, in particular the unsubstituted or singly or several times substituted phenyl radical, the pyridine radical or the thiophene radical. In the same manner, there are also suitable poly-nuclear aromatic or heteroaromatic ring systems, among them also those which are partially hydrogenated, for example naphthalene, benzofurane, dihydrobenzofurane, chromane, chromene or homochromane, quinoline, benzthiophene.

As the member Y in the above formula, there may be used, besides a single chemical bond, in particular lower hydrocarbon chains. These may be straight or branched and also substituted or interrupted by a heteroatom.

The member Z is in the first instance hydrogen, but a substitution of the central phenyl nucleus by one or several substituents is not excluded.

In the tests for the activity of the compounds of the invention, especially those of the general formula II showed outstanding properties.

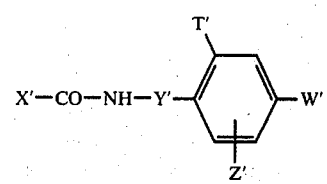

In the above formula:

T' represents hydrogen or halogen, preferably chlorine or bromine,

W' represents a carboxyl group, an ester or a salt thereof,

X' represents (a) a phenyl radical which may carry at any positions the substituents R, $R_1$ and $R_2$, R being hydrogen, alkyl, alkoxy, alkenoxy, alkoxy-alkoxy, phenoxy, halogen, amino, alkylamino, anilino or trifluoromethyl, and $R_1$ and $R_2$, independently of each other, each being hydrogen, alkyl, alkoxy or halogen;

(b) ring systems of the formula III

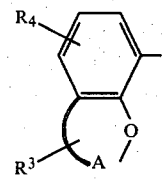

in which $R_3$ represents hydrogen or methyl, and $R_4$ represents hydrogen, alkyl, alkoxy or halogen in the m- or p-position to the CONH-group, and A represents a hydrocarbon chain of 2 to 4 carbon atoms;

(c) a quinoline radical of the formula IV

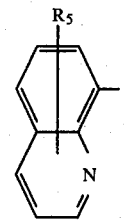

in which $R_5$ represents hydrogen, methyl, methoxy or halogen, or (d) a thiophene radical of the formula V

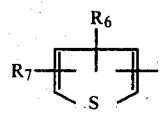

in which $R_6$ and $R_7$, independently of each other, each represent hydrogen, alkyl, alkoxy or halogen;

(e)

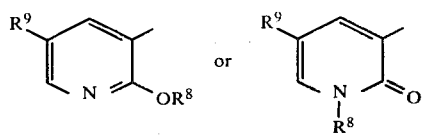

in which $R^8$ represents lower alkyl and $R^9$ represents halogen, preferably chlorine or bromine, Y' represents a single chemical bond or a hydrocarbon radical of 1 to 3 carbon atoms, and Z' represents hydrogen, halogen, alkyl or alkoxy, alkoxy-alkoxy or alkenyloxy.

Alkyl or alkenyl and the alkyl portions in alkoxy, alkenoxy, alkoxy-alkoxy and alkylamino in the sense of the above definitions are straight chain or branched hydrocarbon radicals having not too large a number of carbon atoms. It has been found that the members which contain up to 6 carbon atoms showed the best activity. Halogen in the above sense is in the first instance chlorine and bromine, but it may also be fluorine, especially if X' is a phenyl radical. The corresponding iodine compounds are, in general, also active, but their use is less advisable.

As the bridging member Y', the hydrocarbon bridges with 2 carbon atoms, which themselves may be substituted, also by alkyl groups, are preferably used. Accordingly, the group —$CH_2$—$CH_2$— and the group —$CH(CH_3)$—$CH_2$— are particularly preferred. Less preferred are the other straight chain or branched hydrocarbon bridges containing up to 3 carbon atoms.

The present invention furthermore relates to a process for preparing the above-specified compounds of the invention, which process comprises (a) reacting an amino compound of the general formula

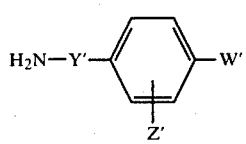

or its formyl compound with a reactive derivative of the acid X'COOH, and optionally splitting off the formyl radical;

(b) in a compound of the general formula

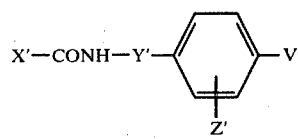

in which V represents a radical which is convertible into a carboxyl group, converting said radical into a carboxyl group, (c) replacing the sulfur atom by an oxygen atom in compounds of the general formula

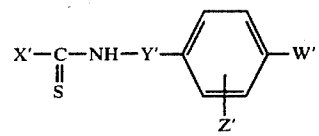

(d) hydrolyzing compounds of the general formula

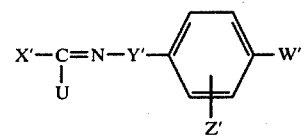

in which U represents low molecular alkoxy, low molecular alkylthio or halogen, or (e) alkylating in compounds of the general formula

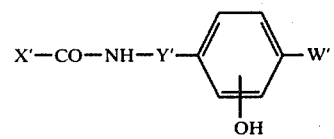

the hydroxy group or a hydroxy group present in the radical X', or (f) rearranging a nitrone of the formula

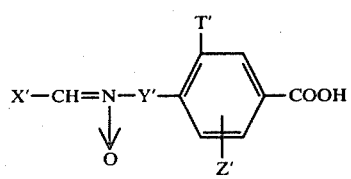

to an acid amide;

and optionally converting the compound obtained into a free benzoic acid or an ester or salt thereof.

The amino compounds serving as starting materials for method (a) are known and may be prepared without difficulty according to methods known for analogous compounds.

These amino compounds are reacted, preferably in the presence of bases, with reactive derivatives of the acid X'—COOH, for example with its halides, anhydrides, mixed anhydrides, azides or esters.

The starting substances for the method (b) may be obtained by acylating an amine of the general formula

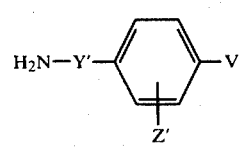

with a radical X'CO or acylating, for example a compound of the general formula

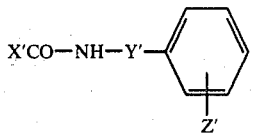

Depending on the nature of the group V, they may be converted by suitable reactions into the compounds of the invention. Such suitable reactions may be, for example a hydrolysis if the substituent V is an amide, a nitrile, an acid halide or a keto-acid, or a hydrazide. Oxydative conversion is used, for example if V represents an alcohol-, aldehyde- or acyl-grouping. If V is halogen, it can be transformed into a carboxyl group by a Grignard reaction.

The starting substances for method (c) may be obtained, for example by reacting an amino compound of the formula

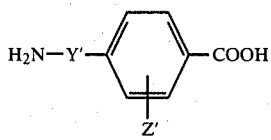

or its ester or salt with a reactive derivative of a thiocarboxylic acid X'CSOH. These thioamides may be desulfurized according to methods used for similar compounds, in particular those of the sulfonyl-urea series, the treatment with hydrogen peroxide or sodium peroxide having proved to be especially suitable.

The starting substances for method (d) may be obtained, for example by methylating the thioamides mentioned under (c), preferably their esters, with diazomethane. They are hydrolyzed in an acid or alkaline medium, the alkaline hydrolysis being preferred.

Etherification of the hydroxyl groups according to method (e) is effected according to known methods, for example by the reaction with dialkyl sulfate or alkyl- or aralkyl-halide.

Compounds of the general formula II in which X' represents a phenyl group which is substituted by an amino group can be obtained from the corresponding nitro-compounds by reduction.

The compounds of the invention have a blood-sugar lowering activity. This activity can be observed by feeding the compounds as such, their salts or esters, in doses of 10 to 400 mg, preferably about 100 mg/kg, to normally fed rabbits and determining the blood sugar level over a prolonged period of time according to the known method of Hagedorn-Jensen or with the aid of an auto-analyzer.

The compounds of the invention shall be used preferably for the preparation of orally administrable compositions having blood sugar lowering action for the treatment of diabetes mellitus and may be administered as such or, optionally, in the form of their salts or esters, or in the presence of substances which provoke salt formation. For the salt formation, for example alkaline substances such as alkali metal or alkaline earth metal hydroxides, carbonates or bicarbonates may be used.

As medicinal compositions, there are preferably used tablets which contain, in addition to the products of the invention, the usual carriers, excipients and adjuvants such as talc, starch, lactose, tragacanth or magnesium stearate.

A composition containing the compounds of the invention as active substance, for example a tablet or a powder, with or without additions is suitably brought into an appropriate dosage unit form. As the dose, such a dose is chosen which is adapted to the activity or potency of the active substance used and to the effect desired. Suitably, the dose per dosage unit is about 0.1 to 2 g, preferably 0.5 to 1 g, but higher or smaller dosage units may also be used which, if desired or required, are divided or multiplied before administration.

The benzoic acid derivatives of the invention may be used for the treatment of diabetes mellitus either alone or in combination with other oral antidiabetics. As such, there may used not only the blood sugar lowering sulfonyl-ureas, but also compounds of different chemical structure, for example biguanides, in particular the phenylethyl-biguanide or the dimethyl-biguanide.

The following Examples describe some of the numerous methods which may be used for the synthesis of the compounds of the invention.

EXAMPLE 1

4-(2-<3-Chloro-benzamido>-ethyl)-benzoic acid 50 ml of a 1-molar solution of 4-(2-aminoethyl)-benzoic acid-sodium, which contained, in addition, 0.05 mole of sodium acetate and which had been prepared by saponification of 4-(2-acetylaminoethyl)-benzoic acid with sodium hydroxide solution, was combined with 50 ml of acetone and then with the solution of 9 g of 3-chlorobenzyl chloride in a small amount of acetone. The whole was stirred for about 1 hour, water and hydrochloric acid were added, filtered off with suction and the product was recrystallized from a mixture of water and isopropanol. The 4-(2-<3-chloro-benzamido>-ethyl)-benzoic acid obtained was found to melt at 200° to 202° C.

In analogous manner, there were obtained:
4-(2-<4-chloro-benzamido>-ethyl)-benzoic acid; M.p. 242°–244° C. (from dilute ethanol),
4-(2-benzamido-ethyl)-benzoic acid, M.p. 217°–219° C. (from dilute methanol),
4-(2-<2-methoxy-benzamido>-ethyl)-benzoic acid, M.p. 153°–155° C. (from dilute methanol),
4-(2-<3-methoxy-benzamido>-ethyl)-benzoic acid, M.p. 170°–172° C. (from dilute methanol),
4-(2-<3-methyl-benzamido>-ethyl)-benzoic acid, M.p. 179°–181° C. (from dilute methanol),
4-(2-<2-n-butoxy-benzamido>-ethyl)-benzoic acid, M.p. 164°–165° C. (from ethanol),
4-(2-<2-n-pentyloxy-benzamido>-ethyl-benzoic acid, M.p. 130°–131° C. (from ethanol),
4-(2-<2-anilino-benzamido>-ethyl)-benzoic acid, M.p. 165°–167° C. (from dilute methanol),
4-(2-<2-methoxy-5-methyl-benzamido>-ethyl)-benzoic acid, M.p. 148°–150° C. (from dilute isopropanol),
4-(2-<5-chloro-2-methoxy-benzamido>-ethyl)-benzoic acid, M.p. 170°–172° C. (from dilute methanol),
4-(2-<5-chloro-2-n-propyloxy-benzamido>-ethyl)-benzoic acid, M.p. 156°–157° C. (from ethyl acetate),
4-(2-<2-n-butyloxy-5-chloro-benzamido>-ethyl)-benzoic acid, M.p. 166° C. (from ethanol),
4-(2-<5-chloro-2-n-pentyloxy-benzamido>-ethyl)-benzoic acid, M.p. 170°–171° C. (from ethanol), 4-(2-<5-chloro-2-n-octyloxy-benzamido>-ethyl)-benzoic acid, M.p. 156°–158° C. (from ethanol), 4-(2-<2-allyloxy-5-chloro-benzamido>-ethyl)-benzoic acid, M.p. 149°–151° C. (from ethanol), 4-(2-<5-chloro-2-methoxyethoxy-benzamido>-ethyl)-benzoic acid, M.p. 144° C. (from ethanol), 4-(2-<5-chloro-2-phenoxy-benzamido>-ethyl)-benzoic acid, M.p. 172°–173° C. (from methanol), 4-(2-<3-chloro-2-methoxy-benzamido>-ethyl)-benzoic acid, M.p. 145° C. (from ethanol), 4-(2-<4-chloro-2-methoxy-benzamido>-ethyl)-benzoic acid, M.p. 184°–186° C. (from ethanol), 4-(2-<3,5-dichloro-benzamido>-ethyl)-benzoic acid, M.p. 260°–262° C. (from dilute methanol), 4-(1-<5-chloro-2-methoxy-benzamido>-ethyl)-benzoic acid, M.p. 212°–214° C. (from dilute methanol), 4-(2-<5-chloro-2-methoxy-benzamido>-propyl)-benzoic acid, M.p. 153°–154° C. (from ethanol), 4-(2-<2-ethoxy-5-chloro-benzamido>-propyl)-benzoic acid, M.p. 180°–182° C. (from dilute methanol), 4-(2-<5-bromo-2-methoxy-benzamido>-ethyl)-benzoic acid, M.p. 169°–172° C. (from isopropanol), 4-(2-<3,5-dichloro-2-methoxy-benzamido>-ethyl)-benzoic acid, M.p. 173°–175° C. (from ethanol), 4-(2-<6-chloroquinoline-8-carboxamido>-ethyl)-benzoic acid, M.p. 206°–208° C. (from dilute ethanol), 4-(2-<6-chloro-chromane-8-carboxamido>-ethyl)-benzoic acid, M.p. 181°–183° C. (from dilute methanol), 4-(2-<5-chloro-2-methyl-benzo[b]furane-7-carboxamido>-ethyl)-benzoic acid, M.p. 214°–216° C. (from dilute methanol), 4-(2-<5-chloro-3-methoxy-thiophene-2-carboxamido>-ethyl)-benzoic acid, M.p. 186°–187° C. (from dilute ethanol), 4-(2-<5-chloro-3-methoxy-thiophene-2-carboxamido>-propyl)-benzoic acid, M.p. 165° C. (from dilute methanol), 4-(2-<2-octyloxy-benzamido>-ethyl)-benzoic acid, M.p. 113° C. (from ethanol), 4-(3-chloro-benzamidomethyl)-benzoic acid, M.p. 210°–212° C. (from dilute methanol), 4-(5-chloro-2-methoxy-benzamidomethyl)-benzoic acid, M.p. 208°–210° C. (from dilute methanol), 4-(5-bromo-2-methoxy-benzamidomethyl)-benzoic acid, M.p. 217°–219° C. (from dilute methanol), 4-(2-ethoxy-5-chloro-benzamido)-3-methyl-benzoic acid, M.p. 230° C. (from ethanol), 4-(2-ethoxy-5-chloro-benzamido)-2-methyl-benzoic acid, M.p. 237° C. (from ethanol), 4-(2-ethoxy-5-chloro-benzamido)-2-methoxy-benzoic acid, M.p. 220°–221° C. (from ethanol-DMF), 4-(6-chloro-chromane-8-carboxamido)-2-methoxy-benzoic acid, M.p. 227° C. (from ethanol-DMF), 4-(5-chloro-2-methoxy-benzamido)-2-propoxy-benzoic acid, M.p. 179° C. (from ethanol), 4-(2-<5-chloro-2-methoxy-benzamido>-ethyl)-3-chloro-benzoic acid, M.p. 185°–187° C. (from ethanol), 3-ethoxy-4-(2-<5-chloro-2-methoxy-benzamido>-ethyl)-benzoic acid, M.p. 175° C. (from ethanol), 4-(2-<5-chloro-2-methoxy-benzamido>-ethyl)-3-methoxy-benzoic acid, M.p. 217°–219° C. (from ethanol), 4-(2-<2-butoxy-benzamido>-ethyl)-3-methoxy-benzoic acid, M.p. 115° C. (from ethanol).

The 4-(2-amino-ethyl)-3-substituted benzoic acids required for the 4 last mentioned substance examples were prepared in the following manner:

4-(2-Acetaminoethyl)-benzoic acid was reacted with nitrating acid to 4-(2-acetaminoethyl)-3-nitro-benzoic acid, M.p. 189° C. (from methanol). The following catalytical hydrogenation yielded the 4-(2-acetaminoethyl)-3-aminoethyl)-3-amino-benzoic acid with a melting point of 143° C. (from ethanol/petroleum ether). From this compound, there was obtained by diazotation and Sandmeyer-reaction the 4-(2-acetamino-ethyl)-3-chloro-benzoic acid having a melting point of 150° C. or by boiling up the diazo solution, the 4-(2-acetaminoethyl)-3-chloro-benzoic acid M.p. 222°–223° C. From 4-(2-acetaminoethyl)-3-hydroxy-benzoic acid, there were obtained with dimethyl sulfate or diethyl sulfate, the corresponding 4-(2-acetaminoethyl)-3-methoxy-benzoic acid methyl ester and the 4-(2-acetaminoethyl)-3-ethoxy-benzoic acid ethyl ester.

EXAMPLE 2

4-(2-<6-Chloro-quinoline-8-carboxamido>-ethyl)-benzoic acid 50 ml of a 1-molar solution of 4-(2-amino-ethyl)-benzoic acid sodium, which additionally contained 0.05 mole of sodium acetate, was combined with 50 ml of acetone. To this solution, there was added dropwise, while stirring and cooling with ice, the mixed anhydride of 6-chloro-quinoline-8-carboxylic acid, prepared from 10.3 g of the acid, 5.6 g of triethylamine and 5.2 g of chloroformic acid methyl ester in acetone, the whole was stirred for 1 hour without cooling, water was added, the whole was acidified and the product that had separated was filtered off with suction. After recrystallization from dilute ethanol, the 4-(2-<6-chloro-quinoline-8-carboxamido>-ethyl)-benzoic acid was found to melt at 206°–208° C.

In analogous manner, there were obtained:
the 4-(2-butoxy-4-methyl-benzamido>-ethyl)-benzoic acid, M.p. 156°–158° C. (from dilute methanol),
the 4-(1-<2-allyloxy-5-chloro-benzamido>-ethyl)-benzoic acid, M.p. 192°–194° C. (from dilute ethanol),
the 4-(2-<2,5-dimethoxy-benzamido>-ethyl)-benzoic acid, M.p. 157°–159° C. (from dilute ethanol).

EXAMPLE 3

4-(2-<2-Ethoxy-5-chloro-benzamido>-ethyl)-benzoic acid 10 g of 4-(2-aminoethyl)-benzoic acid hydrochloride were dissolved in 60 ml of 2 N-sodium hydroxide solution and, after addition of 75 ml of acetone, a solution of 11 g of 2-ethoxy-5-chloro-benzoylchloride in 20 ml of acetone was added dropwise, while stirring. Stirring was continued for 2 hours, the mixture was diluted with water, filtered and acidified with dilute hydrochloric acid. After filtration with suction, the product was recrystallized from ethanol. The 4-(2-<2-ethoxy-5-chloro-benzamido>-ethyl)-benzoic acid obtained was found to melt at 180° C.

In analogous manner, there was obtained the 4-(5-chloro-2-methoxy-benzamido)-benzoic acid, M.p. 265°–266° C. (from ethanol-dioxane).

EXAMPLE 4

4-(2-<5-Chloro-2-phenoxy-benzamido>-ethyl)-benzoic acid 5.5 g of 4-(2-aminoethyl)-benzoic acid were suspended in 50 ml of anhydrous pyridine and combined portionwise, while stirring and cooling, with 8.0 g of 5-chloro-2-phenoxy-benzoyl chloride. The whole was heated to 100° C. and stirred for 3 hours at this temperature. After cooling, it was concentrated under reduced pressure, combined with ice-water, filtered with suction and the product was recrystallized from methanol. The 4-(2-<5-chloro-2-phenoxy-benzamido>-ethyl)-benzoic acid was found to melt at 172°–173° C.

In analogous manner, there was obtained the 4-(5-chloro-2-methoxy-benzamido)-2-chloro-benzoic acid, M.p. 271° C. (from ethanol).

EXAMPLE 5

4-(2-<2-Ethylamino-benzamido>-ethyl)-benzoic acid 8.2 g of N-ethyl-isatoic acid anhydride and 7.1 g of 4-(2-aminoethyl)-benzoic acid were heated for 5 hours, while stirring, to 80°–90° C. in 150 ml of dimethylformamide. After cooling, the whole was filtered and the filtrate was diluted with 300 ml of water. The precipitate that had formed was filtered off with suction. The product was dissolved in a solution of sodium bicarbonate and, after filtration with charcoal, precipitated again with dilute acetic acid. After filtration with suction and recrystallization from ethanol, the 4-(2-<2-ethylaminobenzamido>-ethyl)-benzoic acid was found to melt at 209°–211° C.

In analogous manner, there was obtained from N-ethyl-5-chloro-isatoic acid anhydride and 4-(2-aminoethyl)-benzoic acid ethyl ester, the 4-(2-<2-ethylamino-5-chloro-benzamido>-ethyl)-benzoic acid ethyl ester (M.p. 113°–115° C.), which was transformed by alkaline hydrolysis into the 4-(2-<2-ethylamino-5-chloro-benzamido>-ethyl)-benzoic acid, M.p. 245° C. (from ethanol).

EXAMPLE 6

4-(2-<3-Chloro-2-methoxy-benzamido>-ethyl)-benzoic acid methyl ester 5.8 g. of 4-(2-<5-chloro-2-methoxy-benzamido>-ethyl)-benzoyl-chloride (prepared from the corresponding carboxylic acid with thionyl chloride, reacted as crude product) were introduced, while stirring and cooling, in 25 ml of anhydrous methanol. After having heated for 15 minutes on the steam bath, the mixture was concentrated under reduced pressure, dissolved in ethyl acetate, washed with a NaHCO$_3$ solution and water, dried, concentrated again and the residue was crystallized from a mixture of toluene and petroleum ether. The melting point of the 4-(2-<5-chloro-2-methoxy-benzamido>-ethyl)-benzoic acid methyl ester was found to be at 108°–109° C.

In analogous manner, there was obtained by the reaction with anhydrous ethanol the
4-(2-<5-chloro-2-methoxy-benzamido>-ethylbenzoic acid ethyl ester, M.p. 74°–76° C. (from ethanol).

EXAMPLE 7

4-(2-<5-Chloro-2-methoxy-benzamido>-ethyl)-benzoic acid propyl ester 10 g of 4-(2-<5-chloro-2-methoxy-benzamido>-ethyl)-benzoic acid were heated for 5 hours under reflux in 30 ml of n-propanol after addition of 3 ml of concentrated sulfuric acid. After cooling, the mixture was concentrated under reduced pressure, poured into ice-water, extracted twice with ether, the ether phase was washed with a sodium bicarbonate solution and water, dried, concentrated and the residue was recrystallized from a mixture of ethyl acetate and petroleum ether. The 4-(2-<5-chloro-2-methoxy-benzamido>-ethyl)-benzoic acid-n-propyl ester was found to melt at 67°–68° C.

In analogous manner, there was obtained
with isopropanol: the 4-(2-<5-chloro-2-methoxy-benzamido>-ethyl)-benzoic acid-isopropyl ester, M.p. 66°–67° C. (from a mixture of ethyl acetate and petroleum ether);

with n-butanol: the 4-(2-<5-chloro-2-methoxy-benzamido>-ethyl)-benzoic acid-n-butyl ester, M.p. 58°–60° C. (from a mixture of ethyl acetate and petroleum ether);

from 4-(2-<2-n-butyloxy-benzamido>-ethyl)-benzoic acid with ethanol: the 4-(2-<2-n-butyloxy-benzamido>-ethyl)-benzoic acid ethyl ester, M.p. 55°–56° C. (from ethyl acetate and petroleum ether).

EXAMPLE 8

4-(2-<2-Ethoxy-5-chloro-benzamido>-ethyl)-benzoic acid methyl ester 10.5 g of 4-(2-aminoethyl)-benzoic acid methyl ester-hydrochloride were suspended in 40 ml of dioxane and 20 ml of acetone and the suspension was combined with 8 ml of pyridine. To this suspension, a solution of 10 g of 2-ethoxy-5-chloro-benzoyl chloride in a small amount of acetone was added dropwise, while stirring, and the whole was heated for 2 hours under reflux. After cooling, the mixture was concentrated under reduced pressure, combined with ice-water, filtered with suction, stirred with dilute hydrochloric acid and with a NaHCO$_3$ solution and the resulting product was again filtered off with suction and recrystallized from ethanol. The 4-(2-<2-ethoxy-5-chloro-benzamido>-ethyl)-benzoic acid methyl ester obtained was found to melt at 110° C.

In analogous manner, there was obtained the 4-(2-<5-chloro-2-phenoxy-benzamido>-ethyl)-benzoic acid methyl ester, M.p. 79°–81° C. (from petroleum ether); and from 4-(2-aminoethyl)-benzoic acid . hydrochloride: the 4-(2-<2-ethoxy-5-chloro-benzamido>-ethyl)-benzoic acid ethyl ester, M.p. 79°–80° C. (from ethanol).

EXAMPLE 9

4-(2-<5-Chloro-2-methoxy-benzamido>-ethyl)-benzoic acid 59 g of 4-(2-<5-chloro-2-methoxy-benzamido>-ethyl)-acetophenone (M.p. 103°–105° C., prepared by acetylation of 5-chloro-2-methoxy-N-(2-phenylethyl)-benzamide in dichloroethane with acetyl chloride-/AlCl$_3$) was added dropwise to a solution cooled to 0° C. of 71 g of caustic soda in 380 ml of water and which had been combined with 27.4 ml of bromine, and the whole was stirred for 3 hours at room temperature. Then, 1 liter of water was added, the mixture was filtered and the filtrate was acidified with dilute hydrochloric acid. The product that had precipitated was filtered off with suction and recrystallized from dilute methanol. M.p. 170°–172° C.

EXAMPLE 10

4-(2-<2-Ethoxy-5-chloro-benzamido>-ethyl)-benzoic acid 3.8 g of 4-(2-<2-ethoxy-5-chloro-benzamido>-ethyl)-benzoic acid ethyl ester, prepared according to Example 8, were heated for 2 hours on the steam bath in 10 ml of 2 N-sodium hydroxide solution and 50 ml of ethanol. After cooling, the mixture was concentrated under reduced pressure, the residue was dissolved in water, the solution was filtered and acidified with 2 N-hydrochloric acid. After separation of the precipitate by filtration, it was recrystallized from ethanol. The 4-(2-<2-ethoxy-5-chloro-benzamido>-ethyl)-benzoic acid was found to melt at 180° C.

EXAMPLE 11

4-(2-<5-Chloro-2-methoxy-benzamido>-ethyl)-2-methoxybenzoic acid 4 g of 4-(2-aminoethyl)-2-methoxy-benzoic acid (prepared by catalytical hydrogenation of 4-cyanomethyl-2-methoxy-benzoic acid in methanol in the presence of Raney nickel at 50° C., 100 atmospheres gauge pressure hydrogen) were combined, as crude product, with 50 ml of acetone and 4–5 g of sodium acetate in a small amount of water. Then, 4.3 g of 5-chloro-2-methoxy-benzoyl chloride in a small amount of acetone was added dropwise, while stirring and cooling with ice, the mixture was stirred for 1 hour, combined with water and hydrochloric acid, filtered with suction, the product was dissolved and precipitated from dilute ammonia and recrystallized from a mixture of water and methanol. The 4-(2-<5-chloro-2-methoxy-benzamido>-ethyl)-2-methoxy-benzoic acid was found to melt at 159°–162° C.

In analogous manner, there were obtained:
the 4-(2-<2-butoxy-5-chloro-benzamido>-ethyl)-2-methoxy-benzoic acid, M.p. 100°–102° C. (from dilute methanol),
the 4-(2-<5-bromo-2-methoxy-benzamido>-ethyl)-2-methoxy-benzoic acid, M.p. 147°–149° C. (from dilute ethanol),
the 4-(2-<5-bromo-2-methoxy-nicotinamido>-ethyl)-2-methoxy-benzoic acid, M.p. 94°–96° C. (from dilute ethanol).

In analogous manner, there were obtained from the mixed anhydride obtained using the acid, triethylamine and chloroformic acid ethyl ester:
the 4-(2-<5-chloro-2-propoxy-benzamido>-ethyl)-2-methoxy-benzoic acid, M.p. 120°–122° C. (from dilute methanol),
the 4-(2-<5-chloro-2-(2-methoxy-ethoxy)-benzamido>-ethyl)-2-methoxy-benzoic acid, M.p. 132°–133° C. (from dilute methanol),
the 4-(2-<6-chloro-quinoline-8-carboxamido>-ethyl)-2-methoxy-benzoic acid, M.p. 170°–172° C. (from dilute methanol),
the 4-(2-<2-allyloxy-5-chloro-benzamido>-ethyl)-2-methoxy-benzoic acid, M.p. 126°–128° C. (from dilute methanol),
the 4-(2-<2,5-dimethoxy-benzamido>-ethyl)-2-methoxy-benzoic acid, M.p. 155°–157° C. (from dilute methanol),
the 4-(2-<2-ethoxy-5-chloro-benzamido>-ethyl)-2-methoxy-benzoic acid, M.p. 154°–156° C. (from dilute methanol),
the 4-(2-<6-chloro-chromane-8-carboxamido>-ethyl)-2-methoxy-benzoic acid, M.p. 165°–167° C. (from dilute methanol),
the 4-(2-<3,5-dichloro-benzamido>-ethyl)-2-methoxy-benzoic acid, M.p. 158°–160° C. (from dilute methanol).

EXAMPLE 12

2-Ethoxy-4-(2-<5-chloro-2-methoxy-benzamido>-ethyl)-benzoic acid

A solution of 5.1 g of 5-chloro-2-methoxy-benzoyl chloride in 30 ml of acetone was introduced dropwise, while stirring and cooling and in the presence of sodium acetate, into a solution of 0.025 mole of 2-ethoxy-4-(2-aminoethyl)-benzoic acid sodium (obtained by side chain bromination of 2-ethoxy-4-methylbenzoic acid, conversion of the 2-ethoxy-4-(bromo-methyl)-benzoic acid, M.p. 108°–110° C., into the 2-ethoxy-4-(cyanomethyl)-benzoic acid, M.p. 113°–116° C., and reduction of this compound in ammonia/methanol on Raney nickel to the amino compound) in about 40 ml of water, the whole was stirred for 1 hour at room temperature, the acetone was removed under reduced pressure, the aqueous solution was acidified, the reaction product that had precipitated was separated and re-precipitated from dilute ammonia. After recrystallization from dilute methanol, the 2-ethoxy-4-(2-<5-chloro-2-methoxy-benzamido>-ethyl)-benzoic acid so obtained was found to melt at 115°–117° C.

In analogous manner, there were obtained, using the mixed anhydride:
the 2-ethoxy-4-(2-<6-chloro-chromane-8-carboxamido>-ethyl)-benzoic acid, M.p. 184°–186° C. (from dilute ethanol),
the 2-ethoxy-4-(2-<2-allyloxy-5-chloro-benzamido>-ethyl)-benzoic acid, M.p. 73° C.–75° C. (from ethyl acetate-petroleum ether),
the 2-ethoxy-4-(2-<2-ethoxy-5-chloro-benzamido>-ethyl)-benzoic acid, M.p. 111°–112° C. (from diisopropyl ether/isopropanol),
4-(2-<2-ethoxy-5-chloro-benzamido>-ethyl)-2-ethoxy-benzoic acid, M.p. 111°–112° C. (from diisopropyl ether/isopropanol),
4-ethoxy-4-(2-<2-butoxy-5-chloro-benzamido>-ethyl)-benzoic acid, M.p. 88°–90° C. (from dilute isopropanol), 2-butoxy-4-(2-<5-chloro-2-methoxy-benzamido>-ethyl-benzoic acid, M.p. 98°–100° C. (from dilute methanol).

EXAMPLE 13

4-(2-<5-Chloro-2-methoxy-benzamido>-ethyl)-5-chloro-2-methoxy-benzoic acid 3 g of sulfuryl chloride were added dropwise, while stirring at room temperature, to 4.6 g of 4-(2-aminoethyl)-2-methoxy-benzoic acid - HCl (M.p. 221° C., with decomposition) in 100 ml of glacial acetic acid. The reaction mixture was then heated to 60° C. and kept for 6 hours at this temperature. The glacial acetic acid was removed by distillation under reduced pressure, the residue was treated with isopropanol and filtered off with suction. The 4-(2-aminoethyl)-5-chloro-2-methoxy-benzoic acid hydrochloride was found to melt at 218°–220° C. (decomposition).

2.5 g of hydrochloride were dissolved in 25 ml of acetone and 0.8 g of NaOH in 20 ml of water. To this solution, there were added 2 g of 5-chloro-2-methoxy-benzoyl chloride in 20 ml of acetone and the whole was stirred for 1 hour. Then, water and dilute hydrochloric acid were added and the product was recrystallized from methanol. The 4-(2-<5-chloro-2-methoxy-benzamido>-ethyl)-5-chloro-2-methoxy-benzoic acid so obtained was found to melt at 171°–173° C.

In analogous manner, there were obtained:
the 4-(2-<2-ethoxy-5-chloro-benzamido>-ethyl)-5-chloro-2-methoxy-benzoic acid, M.p. 128°–130° C. (from ethanol),
the 4-(2-<5-chloro-2-propoxy-benzamido>-ethyl)-5-chloro-2-methoxy-benzoic acid, M.p. 139°–141° C. (from dilute ethanol),
the 4-(2-<2-butoxy-5-chloro-benzamido>-ethyl)-5-chloro-2-methoxy-benzoic acid, M.p. 129°–131° C. (from dilute methanol),
the 4-(2-<2-ethoxy-4-methyl-benzamido>-ethyl)-5-chloro-2-methoxy-benzoic acid, M.p. 146°–148° C. (from dilute methanol),
the 4-(2-<6-chloro-quinoline-8-carboxamido>-ethyl)-5-chloro-2-methoxy-benzoic acid, M.p. 198°–201° C. (from methanol/dioxane),
the 4-(2-<5-chloro-2-methoxy-benzamido>-ethyl)-2-butoxy-5-chloro-benzoic acid, M.p. 114°–116° C. (from dilute methanol).

In analogous manner, there was obtained from the 4-(2-aminoethyl)-2-methoxy-benzoic acid hydrochloride by bromination in glacial acetic acid the 4-(2-aminoethyl)-5-bromo-2-methoxy-benzoic acid salt and therefrom, by reaction with 5-chloro-2-methoxy-benzoyl chloride,
the 5-bromo-4-(2-<5-chloro-2-methoxy-benzamido>-ethyl)-2-methoxy-benzoic acid, M.p. 176°–178° C. (from methanol).

EXAMPLE 14

2-Ethoxy-5-bromo-4-(2-<5-chloro-2-methoxy-benzamido>-ethyl)-benzoic acid 1.9 g of 2-ethoxy-4-(2-<5-chloro-2-methoxy-benzamido>-ethyl)-benzoic acid were dissolved in 20 ml of glacial acetic acid. The quantity on the point of a spatula of iron powder was added and a solution of 1 g of bromine in 10 ml of glacial acetic acid was slowly added dropwise. After termination of the dropwise addition, the mixture was stirred for half an hour at 50° C., filtered after cooling, combined with water, the substance that had precipitated was filtered off with suction and recrystallized from dilute methanol. The 2-ethoxy-5-bromo-4-(2-<5-chloro-2-methoxy-benzamido>-ethyl)-benzoic acid so obtained was found to melt at 155°–157° C.

EXAMPLE 15

2-Allyloxy-4-(2-<5-chloro-2-methoxy-benzamido>-ethyl)-benzoic acid 13.6 g of 4-(2-<5-chloro-2-methoxy-benzamido>-ethyl)-2-hydroxy-benzoic acid ethyl ester, M.p. 88°–89° C., (prepared by treatment of 4-(2-aminoethyl)-2-methoxy-benzoic acid. HCl with hydrobromic acid/glacial acetic acid, reaction of the resulting 4-(2-<5-chloro-2-methoxy-benzamido>-ethyl)-2-hydroxy-benzoic acid with ethanol/HCl) were dissolved in 75 ml of DMF and combined with 1.2 g of sodium hydride/80% strength in white oil. The whole was stirred for half an hour, 4.4 g of allyl bromide were added and stirring was continued for 4 hours at 65° C. The dimethylformamide was then eliminated by distillation under reduced pressure, the residue was dissolved in ether, washed with sodium hydroxide solution and water, the ether solution was concentrated by evaporation and the residue was hydrolyzed by heating with 100 ml of 10% sodium hydroxide solution in the presence of a small amount of ethanol. After cooling, the solution was acidified, the substance that had precipitated was re-precipitated from ammonia with the aid of charcoal and then crystallized from dilute methanol. The 2-allyloxy-4-(2-<5-chloro-2-methoxy-benzamido>-ethyl)-benzoic acid so obtained was found to melt at 122°–123° C.

EXAMPLE 16

4-(2-<5-Bromo-2-methoxy-nicotinamido>-ethyl)-benzoic acid 11.6 g of 5-bromo-2-methoxy-nicotinic acid were dissolved in 200 ml of tetrahydrofurane. After addition of 22 ml of triethylamine, the mixture was cooled to 0° C. and 4.8 ml of chloro-formic acid methyl ester were added dropwise. The mixture was stirred for 1 hour at 0° C., 11.5 g of 4-(2-aminoethyl)-benzoic acid ethyl ester hydrochloride were added and stirring was continued for 1 hour at 0° C. and for 4 hours at room temperature. The mixture was evaporated, the residue was treated with water, sodium bicarbonate solution and acetic acid and recrystallized from a mixture of ethanol and water. The 4-(2-<5-bromo-2-methoxy-nicotinamido>-ethyl)-benzoic acid ethyl ester was found to melt at 69°–70° C.

The ester so obtained was boiled in 25 ml of 2N-sodium hydroxide solution and 50 ml of ethanol for 4 hours. After removal of the alcohol by distillation, the mixture was acidified with dilute acetic acid, filtered with suction and the product was recrystallized from ethanol. The 4-(2-<5-bromo-2-methoxy-nicotinamido>-ethyl)-benzoic acid obtained was found to melt at 142°–143° C.

In analogous manner, there was obtained over the 4-(2-<2-methoxy-nicotinamido>-ethyl)-benzoic acid ethyl ester, M.p. 88°–90° C. (from ethanol),
the 4-(2-<2-methoxy-nicotinamido>-ethyl)-benzoic acid, M.p. 157°–158° C. (from ethanol);
over the 4-(2-<1-butyl-pyridone-(2)-3-carboxamido>-ethyl)-benzoic acid, M.p. 156°–157° C. (from methanol).

EXAMPLE 17

2-Ethoxy-4-(5-chloro-2-methoxy-benzamido)-benzoic acid 10.4 g of 2-ethoxy-4-amino-benzoic acid ethyl ester were suspended in a mixture of 6.8 ml of triethylamine and 200 ml of toluene and 10.3 g of 5-chloro-2-methoxy-benzoyl chloride dissolved in a small amount of toluene were added dropwise. The whole was stirred for 3 hours under reflux and, after cooling, it was washed with water, dilute hydrochloric acid and a sodium bicarbonate solution and dried over sodium sulfate. Upon concentration of the solution under reduced pressure, the 2-ethoxy-4-(5-chloro-2-methoxy-benzamido)-benzoic acid ethyl ester was obtained in the form of a solid product having a crude melting point of 108°–111° C.

The ester so isolated was heated for 3 hours, while stirring, under reflux, in 200 ml of 2N-sodium hydroxide solution after addition of a small amount of ethanol. After cooling and acidification with dilute hydrochloric acid, the whole was filtered with suction and the 2-ethoxy-(5-chloro-2-methoxy-benzamido)-benzoic acid was recrystallized from ethanol. It was found to melt at 188° C.

In analogous manner, there was obtained over the 2-ethoxy-4-(2-ethoxy-5-chloro-benzamido)-benzoic acid ethyl ester, melting point of the crude product 115°-118° C., the 2-ethoxy-4-(2-ethoxy-5-chloro-benzamido)-benzoic acid, melting point 199° C. (from ethanol/DMF);

in analogous manner, there was obtained over the 4-(2-allyloxy-5-chloro-benzamido)-2-methoxy-benzoic acid ethyl ester, M.p. of the crude product 128°-129° C., the 4-(2-allyloxy-5-chloro-benzamido)-2-methoxy-benzoic acid, M.p. 211° C. (from ethanol);

in analogous manner, there was obtained the 4-(2-<4-trifluoromethyl-benzamido>-ethyl)-benzoic acid ethyl ester, M.p. 146°-148° C. (from ethanol).

EXAMPLE 18

4-(2-<2-Amino-4-methyl-benzamido>-ethyl)-benzoic acid 11.5 g of 4-(2-<4-methyl-2-nitro-benzamido>-ethyl)-benzoic acid (prepared in a manner analogous to that described in Example 1 from 4-methyl-2-nitro-benzoyl chloride), M.p. 241° C., were dissolved in hot state in a mixture of 200 ml of concentrated ammonia solution and 300 ml of water and, after addition of a solution of 80 g of iron-(II)-sulfate in 400 ml of water, the whole was heated for 90 minutes on the steam bath. After filtration with suction, the filtrate was acidified with glacial acetic acid, the precipitate was filtered off with suction and recrystallized from ethanol. The 4-(2-<2-amino-4-methyl-benzamido>-ethyl)-benzoic acid was found to melt at 211° C.

In analogous manner, there was obtained from 4-(2-<5-chloro-2-nitro-benzamido>-ethyl)-benzoic acid, M.p. 218° C., the 4-(2-<2-amino-5-chloro-benzamido>-ethyl)-benzoic acid, M.p. 209°-210° C. (from methanol).

We claim:

1. A benzoic acid derivative of the formula

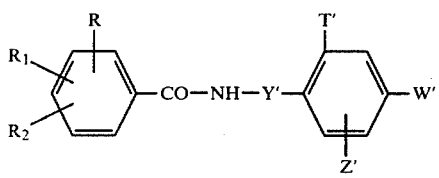

in which

T' is hydrogen or halogen;

W' represents a carboxyl group, an ester or a salt thereof;

R is hydrogen, alkyl, alkoxy, alkenoxy, alkoxyalkoxy, phenoxy, halogen, anilino or trifluoromethyl;

$R_1$ and $R_2$, independently of each other, are hydrogen, alkyl, alkoxy or halogen;

Y' is a hydrocarbon radical of 2 to 3 carbon atoms; and

Z' is hydrogen, halogen or alkyl,

2. A benzoic acid derivative of the formula

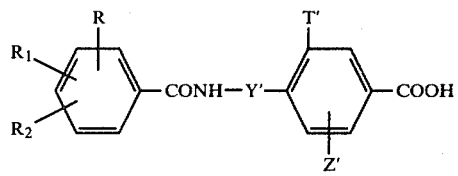

and the esters and physiologically tolerable salts thereof in which

T' is hydrogen, chlorine or bromine;

R is hydrogen, alkyl, alkoxy, alkenoxy, alkoxyalkoxy, phenoxy, halogen, anilino or trifluoromethyl;

$R_1$ and $R_2$, independently of each other, are hydrogen, alkyl, alkoxy or halogen;

Y' is a hydrocarbon radical of 2 to 3 carbon atoms; and

Z' is hydrogen, halogen or alkyl,

3. A compound as defined in claim 2 in which R is alkoxy or alkenoxy, $R_1$ and $R_2$ are hydrogen, alkyl, alkoxy or halogen and Z' is hydrogen or alkyl.

4. The compound of claim 3 which is 4-[2-(5-chloro-2-methoxybenzamido)-ethyl]-benzoic acid.

5. An oral antidiabetic composition containing, as the essential active component, a hypoglycemically effective amount of a compound defined in claim 1.

6. An oral antidiabetic composition containing, as the essential active component, a hypoglycemically effective amount of a compound defined in claim 2.

7. An oral antidiabetic composition containing, as the essential active component, a hypoglycemically effective amount of a compound defined in claim 3.

8. An oral antidiabetic composition containing, as the essential active component, a hypoglycemically effective amount of the compound defined in claim 4.

9. A method of treatment which comprises orally administering to a diabetic patient an effective amount of a compound defined in claim 1.

10. A method of treatment which comprises orally administering to a diabetic patient an effective amount of a compound defined in claim 2.

11. A method of treatment which comprises orally administering to a diabetic patient an effective amount of a compound defined in claim 3.

12. A method of treatment which comprises orally administering to a diabetic patient an effective amount of the compound defined in claim 4.

* * * * *